United States Patent
Leitner et al.

(10) Patent No.: US 6,399,834 B1
(45) Date of Patent: Jun. 4, 2002

(54) METHODS FOR PRODUCING CHIRAL ALDEHYDES

(75) Inventors: Walter Leitner, Mülheim an der Ruhr; Sabine Kainz, Moers; Daniel Koch, Duisburg, all of (DE); Giancarlo Francio, Mesina (IT)

(73) Assignee: Studiengesellschaft Kohle mbH, Mulheim an der Ruhr (DE)

( * ) Notice: Subject to any disclaimer, the term of this patent is extended or adjusted under 35 U.S.C. 154(b) by 0 days.

(21) Appl. No.: 09/831,925
(22) PCT Filed: Nov. 11, 1999
(86) PCT No.: PCT/EP99/08661
§ 371 (c)(1), (2), (4) Date: May 15, 2001
(87) PCT Pub. No.: WO00/31010
PCT Pub. Date: Jun. 2, 2000

(30) Foreign Application Priority Data

Nov. 21, 1998 (DE) .......................... 198 53 748

(51) Int. Cl.[7] .............................. C07C 45/50
(52) U.S. Cl. .................... 568/454; 568/451; 556/18
(58) Field of Search .................. 568/451, 454; 556/18

(56) References Cited

U.S. PATENT DOCUMENTS 5,530,150 A * 6/1996 Takaya et al. ............... 556/18

FOREIGN PATENT DOCUMENTS

| EP | 0 614 903 | 9/1994 |
|----|-----------|--------|
| WO | WO 98 32533 | 7/1998 |

OTHER PUBLICATIONS

Kainz et al., Catalysis Letters, 55: 223–225 (1998).
Francio et al., Chem. Commun., No. 17, pp. 1663–1664 (1999).

* cited by examiner

Primary Examiner—Sreeni Padmanabhan
(74) Attorney, Agent, or Firm—Norris McLaughlin & Marcus

(57) ABSTRACT

The present invention relates to methods for producing chiral aldehydes by the enantioselective hydroformylation of prochiral substrates with the aid of a catalyst consisting of a transition metal and a chiral ligand, characterized in that said chiral ligand is a compound of general formula 1

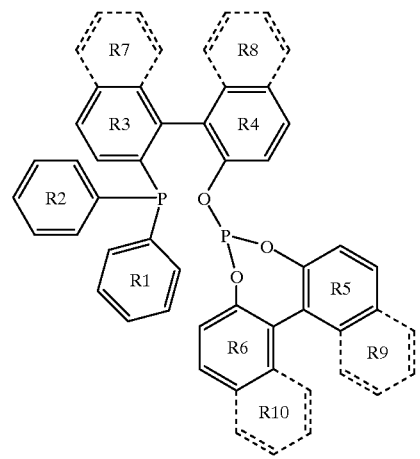

wherein the rings R7–R10 drawn with dotted lines are optional and one or more of rings R1–R6 or R7–R10 are substituted with one or more independently selected substituents of general formula —$(CH_2)_x(CF_2)_yF$ ($x=0–5$; $y=1–12$) or their branched isomers. In particular, the invention relates to the conducting of the mentioned methods in compressed (liquid or supercritical) carbon dioxide as the reaction medium.

12 Claims, No Drawings

METHODS FOR PRODUCING CHIRAL ALDEHYDES

This application is a 371 of PCT/EP99/08661 filed on Nov. 11, 1999.

The present invention relates to methods for producing chiral aldehydes by the enantioselective hydroformylation of prochiral substrates with the aid of a catalyst consisting of a transition metal and a chiral phosphorus-containing ligand which contains aromatic rings substituted with perfluoroalkyl groups.

The addition of hydrogen and carbon monoxide to prochiral C=C double bonds using chiral catalysts (enantioselective hydroformylation) is an efficient method for the synthesis of chiral, non-racemic aldehydes (Catalytic Asymmetric Synthesis, Ed.: I. Ojima, VCH, Weinheim, 1993, p. 273). This reaction type has found great interest, in particular, as a possible access to chiral building blocks for the production of flavoring agents, cosmetics, plant protection agents, food additives (e.g., vitamins), and pharmaceutical agents (Chirality 1991, 3, 355). There may be mentioned, in particular, the preparation of the anti-inflammatory and analgetic drugs ibuprofen and naproxen by the oxidation of the corresponding aldehydes, which can be obtained by enantioselective hydroformylation. Further, chiral aldehydes offer access to α-amino acids, antibiotics based on polyethers and macrocyclic antitumor drugs.

For an efficient enantioselective hydroformylation, the following criteria must be met: 1. high activity of the catalyst; 2. high chemo- and regioselectivity for the formation of the desired aldehyde; 3. high enantioselectivity in favor of the desired enantiomer. The methods known today for enantioselective hydroformylation use catalyst systems which contain a transition metal center in the presence of a chiral coordinated compound (ligand). As the transition metal, rhodium and platinum are mainly used, but other metals including cobalt, iridium or ruthenium also exhibit catalytic activity. As the ligands, chiral phosphorus compounds, above all, have proven useful, the efficiency of the systems being strongly influenced by the structure of the ligands (Chem. Rev. 1995, 95, 2485).

The as yet most efficient catalyst system for enantioselective hydroformylation is based on a rhodium catalyst which contains the ligand (R)-2-(diphenylphosphino)-1,1'-binaphthol-2'-yl (S)-1,1'-binaphthol-2,2'-diyl phosphite, (R,S)-binaphos (Topics in Catalysis 1997, 4, 175; EP 0 614 870 A3) and related ligands (EP 0 684 249 A1, EP 0 647 647 A1). The main drawbacks of the methods relying on this catalyst system include, on the one hand, the limited regioselectivity for the formation of the desired branched isomer in the hydroformylation of vinyl aromatics (see Scheme 1). The regioselectivity with (R,S)-binaphos is, for example, about 88%, and the 12% of linear aldehyde is a worthless by-product which has to be separated off tediously and disposed of. On the other hand, these catalyst systems work with the greatest efficiency only when solvents are used which are toxicologically and ecologically harmful, such as benzene.

Scheme 1:
Reaction scheme for the enantioselective hydroformylation, illustrated for vinylaromatics.

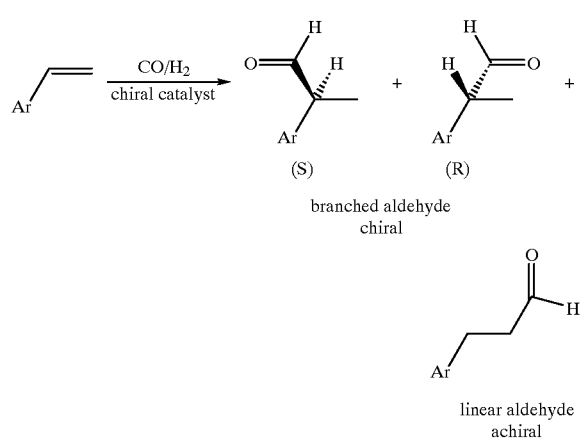

TABLE 1

Synthesis of chiral aldehydes by enantioselective hydroformylation.

| Ex. | Substrate | S/Rh | Ligand | Solvent | Lig/Rh | $p_{H_2, CO}$ [bar] | T [°C.] | $P^0$total [bar] | time t [h] | Conversion [%] | Regioselect. [%] | ee [%] |
|---|---|---|---|---|---|---|---|---|---|---|---|---|
| ref. | styrene | 2000 | binaphos | benzene(0.5 ml) | 4 | 100 | 60 | — | 43 | >99 | 88 | 94(S) |
| 1 | styrene | 2000 | (R, S)-1a | benzene(0.5 ml) | 4 | 100 | 60 | — | 17 | >99 | 92.7 | 90.6(S) |
| 2 | styrene | 1000 | (R, S)-1a | hexane(2.0 ml) | 4 | 100 | 40 | — | 46 | 42 | 95.7 | 90.0(S) |
| 3 | styrene | 786 | (R, S)-1a | CO₂ | 2 | 40 | 45 | 192 | 16 | 42.3 | 93.8 | 93.0(S) |
| 4 | styrene | 2000 | (R, S)-1a | CO₂ | 3 | 40 | 40 | 178 | 66 | 75.4 | 94.8 | 93.6(S) |
| 5 | styrene | 1000 | (R, S)-1a | CO₂ | 2 | 20 | 60 | 156 | 16 | >99 | 92.5 | 90.4(S) |
| 6 | styrene | 1000 | (R, S)-1a | CO₂ | 2 | 60 | 60 | 242 | 16 | 97.6 | 93.0 | 92.0(S) |
| 7 | styrene | 1000 | (R, S)-1a | CO₂ | 2.4 | 40 | 36 | 123 | 62 | 91.6 | 94.8 | 91.8(S) |
| 8 | styrene | 1000 | (R, S)-1a | CO₂ | 2.4 | 40 | 31 | 115 | 62 | 96.5 | 95.6 | 91.8(S) |
| ref. | p-chlorostyrene | 2000 | binaphos | benzene(0.5 ml) | 4 | 100 | 60 | — | 34 | >99 | 87 | 93(+) |
| 9 | p-chlorostyrene | 1000 | (R, S)-1a | CO₂ | 2 | 40 | 40 | 150 | 15 | 89 | 91.9 | 88.4(+) |
| ref. | p-isobutylstyrene | 300 | binaphos | benzene(0.5 ml) | 4 | 100 | 60 | — | 66 | >99 | 88 | 92(S) |

TABLE 1-continued

Synthesis of chiral aldehydes by enantioselective hydroformylation.

| Ex. | Substrate | S/Rh | Ligand | Solvent | Lig/Rh | $p_{H_2, CO}$ [bar] | T [°C.] | $P^0$total [bar] | time t [h] | Conversion [%] | Regioselect. [%] | ee [%] |
|---|---|---|---|---|---|---|---|---|---|---|---|---|
| 10 | p-isobutylstyrene | 1000 | (R, S)-1a | $CO_2$ | 2 | 40 | 40 | 146 | 16 | >99 | 95.5 | 90.1(S) |
| 11 | p-isobutylstyrene | 1000 | (R, S)-1a | $CO_2$ | 2 | 40 | 29 | 115 | 43 | 61.2 | 96.1 | 92.8(S) | ref.: Data from K. Nozaki et al., Topics in Catalysis 1997, 4, 175; J. Am. Chem. Soc. 1997, 119, 4413.

Compressed carbon dioxide in the liquid (liqCO$_2$) or supercritical state (ScCO$_2$) is an interesting solvent for performing catalytic reactions because it is toxicologically and ecologically safe, in contrast to conventional organic solvents. A survey of catalytic reactions in scCO$_2$ is found in Science 1995, 269, 1065. To date, liqCO$_2$ has been employed as a reaction medium only in a few cases, e.g., Angew. Chem. 1997, 109, 2562. However, the ligand (R,S)-binaphos cannot be employed efficiently in compressed carbon dioxide since the enantioselectivity is drastically decreased in the presence of compressed carbon dioxide (S. Kainz, W. Leitner, Catal. Lett., in press).

The use of perfluorinated alkyl chains for increasing the solubility of arylphosphorus ligands in supercritical carbon dioxide and the use of corresponding achiral ligands in the rhodium-catalyzed hydroformylation in scCO$_2$ has been described in the German Offenlegungsschrift DE 197 02 025 A1. However, an increased regioselectivity in favor of the linear achiral aldehyde is found with the ligands described therein. The use of scCO$_2$ is a precondition for achieving high reaction rates, while liqCO$_2$ results in inefficiently slow reactions (D. Koch, W. Leitner, J. Am. Chem. Soc, in press).

We now describe a novel method for producing chiral aldehydes by the enantioselective hydroformylation of prochiral substrates with the aid of a catalyst consisting of a transition metal and a chiral ligand, characterized in that said chiral ligand is a compound of general formula 1

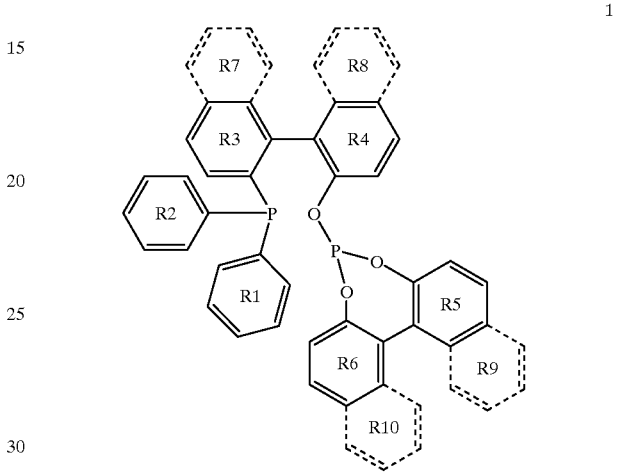

wherein the rings R7–R10 drawn with dotted lines are optional and one or more of rings R1–R6 or R7–R10 are substituted with one or more independently selected substituents of general formula —(CH$_2$)$_x$(CF$_2$)$_y$F (x=0–5; y=1–12) or their branched isomers. The synthetic route for such a ligand is shown in Scheme 2, illustrated for the ligand (R,S)1a.

Scheme 2:
Synthetic route for the chiral ligand 1a [R$_f$ = (CH$_2$)$_2$(CF$_2$)$_6$F] as an example of ligands of general formula 1.

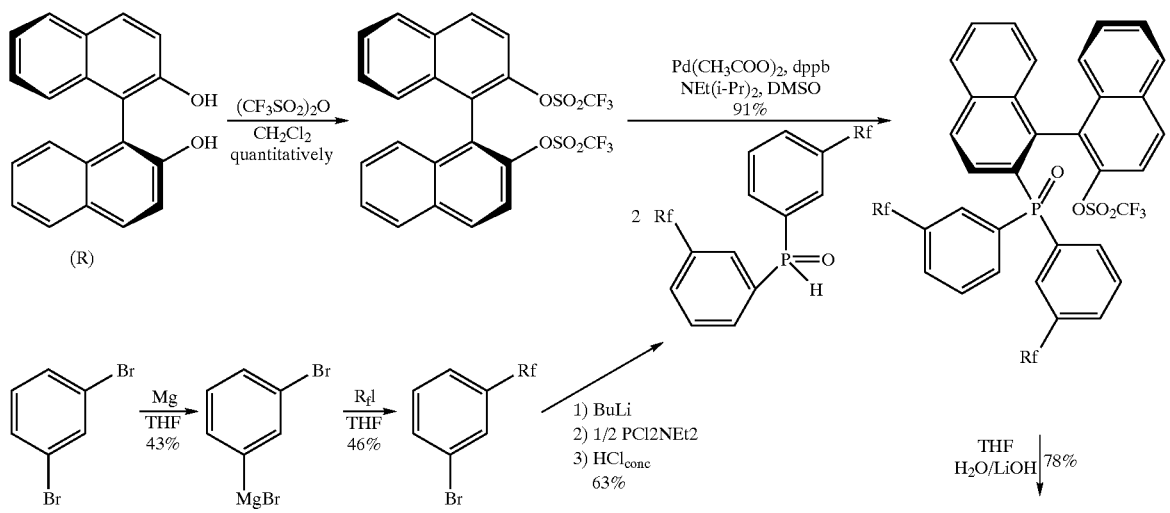

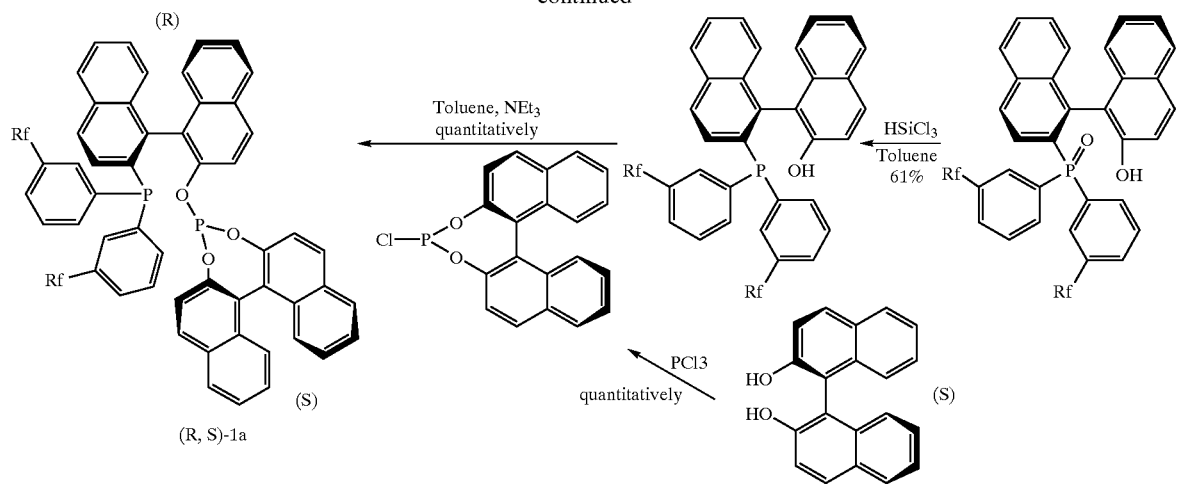

Surprisingly, in the hydroformylation of prochiral substrates, the use of these ligands results in a higher regioselectivity in favor of the branched, chiral aldehyde isomers as compared to a reaction performed with corresponding unsubstituted compounds, but without adversely affecting the enantioselectivity. At the same time, these substituents allow to perform the mentioned processes in compressed carbon dioxide as a reaction medium, whereby the use of toxic or ecologically harmful solvents is avoided. Unexpectedly, the hydroformylation can be performed not only in supercritical $CO_2$ ($scCO_2$), but also in liquid $CO_2$ ($liqCO_2$), which enables working at lower temperatures and pressures during the reaction. Making use of the extractive properties of $CO_2$, the products and catalysts can be separated effectively and carefully, and the catalysts are recovered in an active form.

The catalysts for the enantioselective hydroformylation can be either employed in the form of isolated complex compounds which already contain the chiral ligands of formula 1, or they are formed in situ from a ligand of formula 1 and a suitable metal-containing precursor. A detailed description of possible catalyst systems is found, for example, in Chem. Rev. 1995, 95, 2485. In the present method, compounds or salts of transition metals can be employed as metal components. Preferred are catalysts based on the metals Fe, Co, Ir, Ru, Pt, Rh, especially preferred Pt and Rh. Particularly preferred metal components include, for example, $RhCl_3nH_2O$, $[Rh_2(OAc)_4]$ ($OAc=O(O)CCH_3$)], $[(L)_2Rh(\mu\text{-}Cl)_2Rh(L)_2]$($L$=olefin, CO, $PR_3$ etc.), $[(L)_2Rh(acac)]$(acac=acetylacetonate) or $[(L)_2PtCl_2]/SnCl_2$, without intending that this enumeration should imply a limitation. The optimum molar ratio of ligand/metal depends on the respective system, but should usually be between 1:1 and 10:1, preferably between 1:1 and 4:1.

Possible substrates for the enantioselective hydroformylation using the ligands of general formula 1 include all compounds which contain a prochiral C=C double bond having an appropriate reactivity. Examples of such compounds can be seen from the following group, without intending that the selection of the compounds should imply a limitation to the scope of application: vinylaromatics (e.g., styrene and substituted styrene derivatives, such as chlorobenzene, para-isobutylstyrene or vinylnaphthyl and its derivatives), vinylpyridine, acrylic acid and its derivatives (e.g., α-acetamidoacrylic acid ester), vinyl acetate, vinyl phthalates, allyl acetate, indene, dihydro-2-pyridones, norbornene, and many more. A complete solubility of the substrates and products during the entire duration of the reaction is no necessary precondition for the reaction to proceed effectively when it is performed in compressed $CO_2$. The molar ratio of substrate and catalyst is mainly determined by economical considerations and represents a compromise between the costs for the catalyst and the practically acceptable reaction rate. Therefore, the optimum value may vary within a broad range depending on the substrate and catalyst. With the catalyst, 1a /Rh, ratios of substrate/catalyst of between 100:1 and 100,000:1 are possible, a ratio of between 500:1 and 10,000:1 being preferably used.

The gases $H_2$ and CO can be supplied to the reactor either separately or as a mixture. The partial pressure p of the individual gases is within a range of between 1 and 100 bar, preferably within a range of between 5 and 50 bar. When the reaction is performed in carbon dioxide, the reaction gases can be introduced prior to, after or together with the $CO_2$. The amount of $CO_2$ is selected such that the total pressure at the reaction temperature, $p^0_{total}$, is within a range of between 20 and 500 bar, preferably within a range of between 50 and 350 bar. The reaction temperature may be varied within a broad range and is situated between −20° C. and 100° C., preferably between 20° C. and 60° C. At reaction temperatures below the critical temperature of $CO_2$ ($T_c$=31° C.), there is always a liquid $CO_2$ phase, wherein the total pressure, $p_{total}$, at T<31° C. should preferably be between 50 and 150 bar. At temperatures above the critical temperature (T>31° C.), the phase behavior depends on the substrates employed and the composition of the reaction mixture, and the total pressure, $p^0_{total}$, should be within the preferred range of between 75 and 350 bar. If conducted without carbon dioxide, the reaction is performed either in the absence of an additional solvent or with the use of any organic solvent which does not adversely affect the reaction. Preferred solvents include, for example, pentane, hexane, toluene, benzene, diethyl ether, tetrahydrofuran, chloroform, methylene chloride, perfluorinated hydrocarbons or perfluorinated polyethers.

When the reaction is performed in compressed carbon dioxide, after completion, the product can be separated from the catalyst as described in DE 197 02 025 A1 by extraction with $CO_2$, the catalyst remaining in the reactor in an active and selective form. The combination of reaction and extraction can be realized in a batch, semi-batch or continuous process.

EXPERIMENTAL EXAMPLES

Representative results obtained with the ligand (R,S)-1a are summarized in Table 1 and compared to the comparative values from the previous process with the unsubstituted parent compound ("binaphos"=(R,S)-binaphos) in conventional solvents (data from K. Nozaki et al., Topics in Catalysis 1997, 4, 175; J. Am. Chem. Soc. 1997, 119, 4413).

Enantioselective Hydroformylation in Compressed Carbon Dioxide Examples 3–11

In a steel autoclave equipped with windows, a pressure gauge, one thermoindicator each for the jacket and interior temperatures and two valves (V=11.4 ml), the complex [{(R,S)-1a}Rh(acac)] (3.3 mg, 2×10⁻³ mmol) was charged together with an amount of the ligand (R,S)-1a sufficient to obtain the desired ratio of (R,S)-1a to Rh. Subsequently, the corresponding amount (about 0.2–0.5 ml) of substrate was added (molar ratio of substrate to rhodium=S/Rh). Synthesis gas (CO/H$_2$=1:1) was added under pressure until a pressure of $p_{H_2,co}$ was reached at room temperature. CO$_2$ (about 5–8 g) was filled in with a compressor and heated to the desired reaction temperature T, which provided a pressure $p_{total}$. After the reaction time t, the reactor was cooled down to 0° C., and the pressure was slowly released. To isolate the reaction products, the contents of the reactor was either extracted with scCO$_2$ or taken up in hexane or toluene, filtrated over some silica gel, and the solvent removed by distillation or under vacuum. The conversion, regioselectivity in favor of the branched aldehyde and enantiomeric excess (ee) were determined by gas chromatography (HP 5890 with FID, column: Ivadex 7, injector temp.: 240° C., column temp.: 60–200° C.; detector temp.: 300° C., carrier gas: H$_2$).

Enantioselective Hydroformylation in Other Solvents Examples 1–2

To a mixture of [{(R,S)-1a}Rh(acac)], (R,S)-1a and styrene prepared as described above, the desired amount of solvent was added. Subsequently, synthesis gas was added under pressure until a pressure of $p_{H_2,co}$ was reached, and the solution was heated to the desired reaction temperature T with stirring. After the reaction time t, the reactor was cooled down, and the pressure was released. The reaction solutions were filtered over some silica gel, and the solvent removed under vacuum or by distillation. An analysis was performed as described above.

What is claimed is:

1. A method for producing chiral aldehydes comprising enantioselective hydroformylation of prochiral substrates with the aid of a catalyst consisting of a transition metal and a chiral ligand, wherein said hydroformylation is performed in compressed carbon dioxide as a reaction medium at temperatures of −20° C.<T <100° C. and total pressures of 20 bar<$p°_{total}$<500 bar, and said chiral ligand is a compound of general formula 1

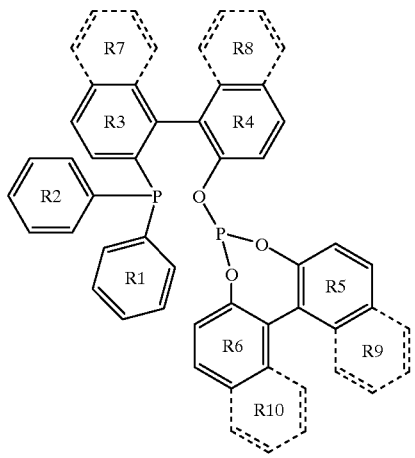

wherein the rings R7–R10 drawn with dotted lines are optional and one or more of rings R1–R6 or R7–R10 are substituted with one or more independently selected substituents of general formula —(CH$_2$)$_x$(CF$_2$)$_y$F(x=0–5; y=1–12) or their branched isomers.

2. The method according to claim 1, wherein said transition metal is Fe, Co, Ir, Ru, Pt or Rh.

3. The method according to claim 2, wherein said transition metal is Pt or Rh.

4. The method according to claim 1, wherein said method is conducted at partial pressures of H$_2$ within a range of p(H$_2$)=1 to 100 bar.

5. The method according to claim 4, wherein said method is conducted at H$_2$ partial pressures of between 5 and 50 bar.

6. The method according to claim 1, wherein said method is conducted at partial pressures of CO within a range of p(CO)=1 to 100 bar.

7. The method according to claim 6, wherein said method is conducted at CO partial pressures of between 5 and 50 bar.

8. The method according to claim 1, wherein said method is conducted at temperatures T of between 20° C. and 60° C.

9. The method according to claim 1, wherein said method is conducted at total pressures of between 50 and 350 bar.

10. The method according to claim 1, wherein a separation of the chiral aldehydes from the catalyst is effected by extraction with supercritical carbon dioxide.

11. The method according to claim 10, wherein the enantioselective hydroformylation and extraction are combined in a batch or semibatch procedure.

12. The method according to claim 10, wherein the enantioselective hydroformylation and extraction are combined in a continuous procedure.

* * * * *

UNITED STATES PATENT AND TRADEMARK OFFICE
CERTIFICATE OF CORRECTION

PATENT NO.   : 6,399,834 B1
DATED        : June 4, 2002
INVENTOR(S)  : Walter Leitner et al.

It is certified that error appears in the above-identified patent and that said Letters Patent is hereby corrected as shown below:

<u>Title page,</u>
Item [75], Inventors, change the place of residence of the fourth inventor from: "Mesina" to -- Messina --

Signed and Sealed this

Eleventh Day of February, 2003

JAMES E. ROGAN
*Director of the United States Patent and Trademark Office*